(12) United States Patent
Inamasu et al.

(10) Patent No.: US 9,552,651 B2
(45) Date of Patent: Jan. 24, 2017

(54) METHOD FOR MONITORING INSIDE A CHAMBER OF A COKE OVEN, MANAGEMENT METHOD FOR A CHAMBER WALL OF A COKE OVEN, AND MONITORING SYSTEM

(75) Inventors: Hironobu Inamasu, Kakogawa (JP); Hideo Matsushita, Kakogawa (JP); Takashi Yoshihara, Kakogawa (JP)

(73) Assignee: KANSAI COKE AND CHEMICALS CO., LTD., Amagasaki-shi (JP)

( * ) Notice: Subject to any disclaimer, the term of this patent is extended or adjusted under 35 U.S.C. 154(b) by 916 days.

(21) Appl. No.: 13/989,707

(22) PCT Filed: Oct. 14, 2011

(86) PCT No.: PCT/JP2011/073725
§ 371 (c)(1),
(2), (4) Date: May 24, 2013

(87) PCT Pub. No.: WO2012/070327
PCT Pub. Date: May 31, 2012

(65) Prior Publication Data
US 2013/0242081 A1    Sep. 19, 2013

(30) Foreign Application Priority Data
Nov. 26, 2010    (JP) .................... 2010-263688

(51) Int. Cl.
*G06K 9/00* (2006.01)
*G06T 7/60* (2006.01)
(Continued)

(52) U.S. Cl.
CPC .............. *G06T 7/602* (2013.01); *C10B 33/10* (2013.01); *C10B 45/00* (2013.01); *G01N 21/954* (2013.01);
(Continued)

(58) Field of Classification Search
CPC ....... C10B 33/10; C10B 45/00; G01N 21/954; G06T 7/0004; G06T 7/0008; G06T 7/602; H04N 7/18
See application file for complete search history.

(56) References Cited

U.S. PATENT DOCUMENTS 5,715,328 A    2/1998    Tsukihara
6,002,993 A  * 12/1999    Naito ................. C10B 41/00
                                                        348/83
(Continued)

FOREIGN PATENT DOCUMENTS

CN         703485       * 11/2005    ............ C10B 29/06
JP      2001-040359     *  7/1999    ............ C10B 41/00
(Continued)

OTHER PUBLICATIONS

International Search Report for PCT/JP2011/073725 dated Dec. 13, 2011.
(Continued)

*Primary Examiner* — Amara Abdi
(74) *Attorney, Agent, or Firm* — Birch, Stewart, Kolasch & Birch, LLP

(57) ABSTRACT

A coke oven monitoring system capable of quantitatively monitoring changes in the state of the furnace walls in a coke oven with good accuracy has: an oven width measurement device (6) that measures the oven width; an in-furnace observation device (7) that photographs the oven walls; and a computer (10) that analyzes oven width data measured by the oven width measurement device, and oven wall image data captured by the in-furnace observation device. The computer is characterized by including: a oven width/oven wall image data extraction unit (10a) that extracts width data and oven wall image data in different extrusion cycles for the
(Continued)

same location of the same kiln; and an oven width/oven wall image data analysis and processing unit (10b) that determines oven wall abnormalities when the oven width data and oven wall image data obtained in the current extrusion cycle have both changed relative to the oven width data and oven wall image data obtained in past extrusion cycles in such a manner as to exceed established values.

A coke oven monitoring system capable of quantitatively monitoring changes in the state of the furnace walls in a coke oven with good accuracy has: an oven width measurement device (6) that measures the oven width; an in-furnace observation device (7) that photographs the oven walls; and a computer (10) that analyzes oven width data measured by the oven width measurement device, and oven wall image data captured by the in-furnace observation device. The computer is characterized by including: a oven width/oven wall image data extraction unit (10a) that extracts width data and oven wall image data in different extrusion cycles for the same location of the same kiln; and an oven width/oven wall image data analysis and processing unit (10b) that determines oven wall abnormalities when the oven width data and oven wall image data obtained in the current extrusion cycle have both changed relative to the oven width data and oven wall image data obtained in past extrusion cycles in such a manner as to exceed established values.

9 Claims, 8 Drawing Sheets

(51) Int. Cl.
| | | |
|---|---|---|
| C10B 33/10 | (2006.01) | |
| C10B 45/00 | (2006.01) | |
| H04N 7/18 | (2006.01) | |
| G06T 7/00 | (2006.01) | |
| G01N 21/954 | (2006.01) | |

(52) U.S. Cl.
CPC ........... *G06T 7/0004* (2013.01); *G06T 7/0008* (2013.01); *H04N 7/18* (2013.01)

(56) References Cited

U.S. PATENT DOCUMENTS

| | | |
|---|---|---|
| 7,630,090 B2 | 12/2009 | Inamasu et al. |
| 2009/0103101 A1 | 4/2009 | Inamasu et al. |
| 2010/0095752 A1* | 4/2010 | Sugiura .................. C10B 29/06 73/104 |

FOREIGN PATENT DOCUMENTS

| | | | |
|---|---|---|---|
| JP | 11-256166 A | 9/1999 | |
| JP | 2001-003058 | * 1/2001 | ............. C10B 29/00 |
| JP | 2008-169274 | * 1/2001 | ............. C10B 29/00 |
| JP | 2001-40359 A | 2/2001 | |
| JP | 2001-294867 A | 10/2001 | |
| JP | 2006-36958 A | 2/2006 | |
| JP | 2007-232471 A | 9/2007 | |
| JP | 2007-332382 A | 12/2007 | |
| JP | 2008-169274 | * 7/2008 | ............. C10B 29/02 |
| JP | 2009-057491 | * 3/2009 | ............. C10B 29/06 |
| JP | 2009-57491 A | 3/2009 | |

OTHER PUBLICATIONS

Office Action issued Mar. 10, 2015, in Taiwan Patent Application No. 100138663, with English translation.
Supplementary European Search Report issued Feb. 12, 2016, in European Patent Application No. 11842518.0.
First Notification of Office Action issued Jan. 24, 2014, in Chinese Patent Application No. 201180056992.4, with English translation.
Notification of Reasons for Rejection issued Sep. 30, 2014, in Japanese Patent Application No. 2010-263688, with English translation.
Second Notification of Office Action issued Sep. 25, 2014, in Chinese Patent Application No. 201180056992.4, with English translation.

* cited by examiner

METHOD FOR MONITORING INSIDE A CHAMBER OF A COKE OVEN, MANAGEMENT METHOD FOR A CHAMBER WALL OF A COKE OVEN, AND MONITORING SYSTEM

TECHNICAL FIELD

The present invention relates to a method for monitoring inside a chamber of a coke oven in which changes in the state of chamber walls in the coke oven can be quantitatively monitored with excellent accuracy, a management method for the chamber wall of the coke oven, and a monitoring system.

BACKGROUND ART

A coke oven is configured by carbonization chambers and combustion chambers that are alternately provided along a coke oven battery. Heat in the combustion chamber transferred to the carbonization chamber dry distills coal charged in the carbonization chamber so as to produce coke.

In this country, because many of the coke ovens have been used for years after the construction, carbon have repeatedly adhered, grown, and been peeled off wall surfaces of the carbonization chambers in the coke ovens. Such aged coke ovens tend to have increased resistance against coke extrusion due to this repetition. The increase in resistance against extrusion may cause troubles in removing coke out of a carbonization chamber. Therefore, monitoring the state of the chamber wall in the coke oven is quite important for safe operation of the oven.

Monitoring the state of chamber walls have been conventionally performed visually, or with use of a permanent chamber width measurement device (see Patent Document 1, for example) or a permanent in-chamber observation device (see Patent Document 2, for example).

However, visual monitoring is difficult to be accurately performed even by an experienced worker, because the worker cannot closely approach the oven having in-chamber temperature as high as about 1,100° C., as well as because a coke oven is configured to have a distance to the back as long as about 15 m while having a chamber width as short as approximately 450 mm, thereby failing to secure a clear visual field.

Even in the case of monitoring with use of the permanent chamber width measurement device or the permanent in-chamber observation device, although an operator checks chamber width data and monitors chamber wall images, such monitoring in the oven is performed along with other tasks. It is, therefore, hard to constantly monitor changes in the state of chamber walls.

PRIOR ART DOCUMENTS

Patent Documents

Patent Document 1: JP-A-2007-232471
Patent Document 2: JP-A-2009-57491

SUMMARY OF THE INVENTION

Problems to be Solved by the Invention

The state of chamber walls changes day by day in the continuous operation of a coke oven. Some incidental change may cause extrusion troubles such as a stuck in a carbonization chamber. There are thus demands for a system that realizes constant monitoring on changes in the state of chamber walls.

The present invention has been achieved in view of the above problems in the conventional method for monitoring inside the chamber. It is an object of the present invention to a method for monitoring inside a chamber of a coke oven in which changes in the state of chamber walls in the coke oven can be quantitatively monitored with excellent accuracy, a management method for the chamber wall of the coke oven, and a monitoring system.

Solutions to the Problems

The present invention provides three modes, namely, a method for monitoring inside a chamber of a coke oven changes in the state of chamber walls in the coke oven, a management method for the chamber wall of the coke oven of managing a tendency in the state of the chamber walls, and a monitoring system.

According to the first mode, a method for monitoring inside a chamber of a coke oven includes:

obtaining pieces of chamber width data and pieces of chamber wall image data in different extrusion cycles at a same location in a same carbonization chamber in a coke oven; and determining an chamber wall abnormality if both of the piece of chamber width data and the piece of chamber wall image data obtained in a current extrusion cycle change so as to exceed predetermined values relatively to the piece of chamber width data and the piece of chamber wall image data obtained in a past extrusion cycle.

The extrusion cycle means a process until it pushes out the coke generated by dry distillation from the carbonization chamber after filling a coal into the carbonization chamber. This process (cycle) is repeated.

The chamber width means a distance between chamber walls.

As a method of determining an chamber wall abnormality, there is provided a method including: calculating and numerically converting a finite difference between the piece of chamber width data in the current extrusion cycle and the piece of chamber width data in the past extrusion cycle and a finite difference between an area of an chamber wall damaged portion in the piece of chamber wall image data in the current extrusion cycle and an area of an chamber wall damaged portion in the piece of chamber wall image data in the past extrusion cycle; and comparing the finite difference value between the pieces of chamber width data with the predetermined value for chamber width data, and comparing the finite difference value between the pieces of chamber wall image data with the predetermined value for chamber wall image data. "Finite difference value" in the present invention corresponds to "the calculated and numerically processed finite difference".

According to the second mode, a management method for the chamber wall of the coke oven includes:

obtaining pieces of chamber width data and pieces of chamber wall image data in different extrusion cycles at a same location in a same carbonization chamber in a coke oven;

numerically converting the pieces of chamber width data and the pieces of chamber wall image data thus obtained and accumulating for the respective extrusion cycles in accumulation means;

setting the piece of chamber width data and the piece of chamber wall image data in specific one of the extrusion cycles accumulated in the accumulation means as pieces of reference data;

numerically converting the piece of chamber width data and the piece of chamber wall image data obtained in one of the extrusion cycles after the specific extrusion cycle and comparing with the pieces of reference data;

accumulating respective comparison results as records for the extrusion cycle, and observing the records thus obtained to grasp a tendency in a state of a chamber wall.

According to the third mode, a monitoring system includes:

a chamber width measurement device that measures a chamber width in a carbonization chamber of a coke oven;

an in-chamber observation device that photographs a chamber wall in the carbonization chamber of the coke oven; and a computer that analyzes chamber width data measured by the chamber width measurement device and chamber wall image data photographed by the in-chamber observation device, the computer including:

a chamber width/chamber wall image data extraction unit that extracts pieces of chamber width data and pieces of chamber wall image data in different extrusion cycles at a same location in a same carbonization chamber; and a chamber width/chamber wall image data analysis and processing unit that determines an chamber wall abnormality if both of the piece of chamber width data and the piece of chamber wall image data obtained in a current extrusion cycle change so as to exceed predetermined values relatively to the piece of chamber width data and the piece of chamber wall image data obtained in a past extrusion cycle.

An extrusion cycle in the present invention indicates a series of the processes from charging coal to extrusion of coke, which is counted as one cycle.

Pieces of past chamber width data (or chamber wall image data) include (a) a piece of data obtained in the last extrusion cycle, (b) a piece of data obtained in the extrusion cycle subsequent to repair, and (c) pieces of data obtained in an arbitrary number of extrusion cycles.

By comparing the piece of data in the current extrusion cycle with the piece of data (a), it is possible to achieve real-time detection of an chamber wall abnormality. By comparing the piece of data in the current extrusion cycle with the piece of data (b) or the pieces of data (c), it is possible to achieve detection of an chamber wall abnormality, as well as to manage a tendency of changes in the state of chamber walls along with increase in the number of extrusion cycles.

Effects of the Invention

The present invention advantageously realizes constant, accurate, and quantitative monitoring on such changes in the state of chamber walls in a coke oven.

MODES FOR CARRYING OUT THE INVENTION

An embodiment of the present invention is described in detail below with reference to the drawings.

Figure 1:
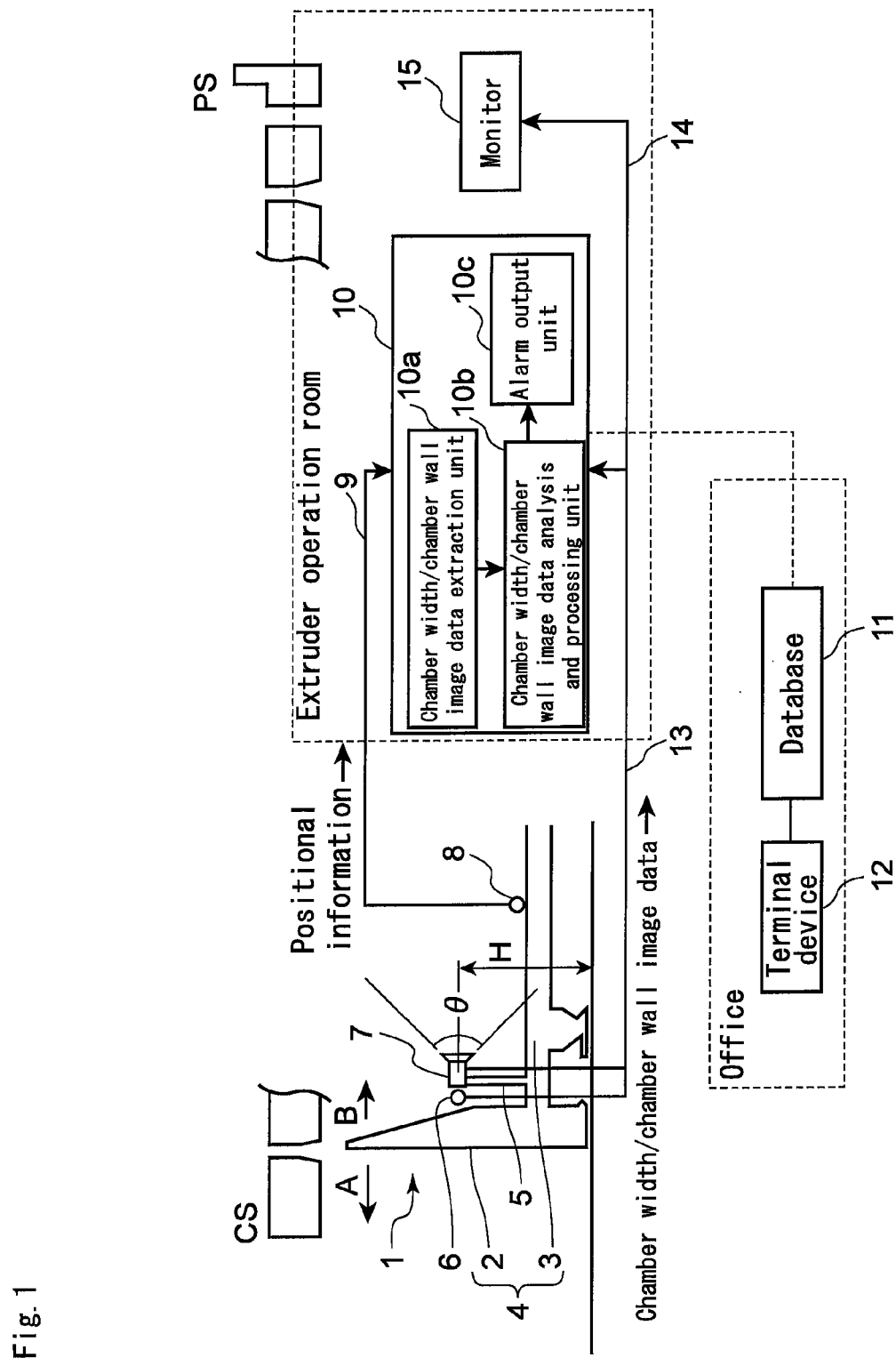
FIG. 1 is a configuration diagram of a monitoring system to see inside a camber of a coke oven according to the present invention.

1. Configuration of the Monitoring System to See Inside the Camber of the Coke Oven FIG. 1 is a configuration diagram of the monitoring system to see inside the camber of the coke oven (hereinafter, abbreviated as the monitoring system) according to the present invention.

In this diagram, a coke extruder 1 includes an extrusion ram 4 that has a ram head 2 and a ram beam 3 for horizontally reciprocating the ram head 2. Coke dry distilled and red heated in a carbonization chamber is extruded by the ram head 2 from a PS (pusher side: coke extruder side) carbonization chamber port to a CS (coke side: coke discharger side) carbonization chamber port.

There is vertically provided a support stand 5 on the ram beam 3 and behind the ram head 2. The support stand 5 is provided with a permanent chamber width measurement device (hereinafter, abbreviated as the chamber width measurement device) 6 and a permanent in-chamber observation device (hereinafter, abbreviated as the in-chamber observation device) 7. The wording "permanent" herein is indicative of being permanently provided to the extrusion ram.

The chamber width measurement device 6 measures a chamber width during coke extrusion (direction A) or while the extrusion ram 4 is returned from the CS carbonization chamber port to the PS carbonization chamber port after completion of the coke extrusion (direction B). The chamber width measurement device 6 may be embodied by a contactless range finder such as a laser displacement sensor.

The in-chamber observation device 7 is equipped with a CCD camera, and sequentially photographs chamber wall images during coke extrusion (direction A) or while the extrusion ram 4 is returned after completion of the coke extrusion (direction B). In the diagram, reference sign θ indicates a view angle of the CCD camera, that is, the (vertical) range photographed by the CCD camera.

The chamber width measurement device 6 and the in-chamber observation device 7 are respectively provided on the support stand 5 so as to measure and observe a location on a wall surface at a certain height (the height of 3.5 m from the bottom of the carbonization chamber in the illustrated example) H.

If such a chamber width measurement devices and in-chamber observation devices are provided at a plurality of heights from the bottom of the carbonization chamber, measurement and observation are enabled in the entire carbonization chamber to quantify measurement results. However, the location of the worst damage in the coke production is predictable from experiences. These devices are thus provided at the height H.

Therefore, it is possible to grasp changes in the state of the chamber walls by measuring and observing only the location on the chamber wall at the height H.

The position of the extrusion ram 4 shifting in the coke oven is detected by an encoder (position detection means) 8 that is attached to the extrusion ram (the ram beam 3 in the illustrated example). Positional information on the extrusion ram 4 outputted from the encoder 8 is transmitted by way of a cable 9 to a computer 10 in an extruder operation room.

The computer 10 is provided with a chamber width/chamber wall image data extraction unit 10a, a chamber width/chamber wall image data analysis and processing unit 10b, and an alarm output unit 10c.

While the extrusion ram 4 is shifted in the carbonization chamber, the chamber width/chamber wall image data extraction unit 10a extracts, for constant distances, chamber width data and chamber wall image data obtained between the PS carbonization chamber port and the CS carbonization chamber port (measurement can be made while the extrusion ram is extruded or withdrawn), with use of positional information outputted from the encoder 8. It is thus possible to obtain chamber width data and chamber wall image data in different extrusion cycles (hereinafter, simply referred to as cycles in some cases) at a predetermined location in the same carbonization chamber.

The chamber width data and the chamber wall image data thus extracted are accumulated in correspondence with the positional information in a database (accumulation means) 11 to be described later. It is possible to read data by accessing the database 11 from a terminal device (computer) 12 in an office. The computer 10 and the database 11 can be connected to each other by wired connection or by wireless connection.

Chamber width data and chamber wall image data outputted respectively from the chamber width measurement device 6 and the in-chamber observation device 7 are transmitted by way of signal/power cables 13 to the computer 10.

Chamber wall image data is also transmitted by way of a signal cable 14 to a monitor 15 in the extruder operation room, so as to enable real-time observation of the state in the carbonization chamber.

The chamber width/chamber wall image data analysis and processing unit 10b analyzes chamber width data and chamber wall image data extracted by the chamber width/chamber wall image data extraction unit 10a, in accordance with a program preliminarily stored.

More specifically, data in the current extrusion cycle and past data (data obtained in the last extrusion cycle, data obtained in an extrusion cycle subsequent to repair, or data obtained in an arbitrary number of extrusion cycles) are compared with each other for respective same positions in the direction of extruding or in the direction of withdrawing the extrusion ram between the PS carbonization chamber port and the CS carbonization chamber port. Each change therebetween is calculated as a finite difference. These data analysis processes are to be detailed later.

The alarm output unit 10c reports abnormalities to an operator in the operation room upon detection, in the analysis results made by the chamber width/chamber wall image data analysis and processing unit 10b, of in-chamber abnormalities such as adhesion, growth, and peeling off of carbon, which lead to increase in power used for extrusion.

2. Data Analysis Method

Described next are the processes of analysis on chamber width data and chamber wall image data.

Assume that emptying a carbonization chamber of removing carbon adhering in the carbonization chamber by repair (once in about 100 to 200 cycles per carbonization chamber) is counted as zero cycle, and extruding once is counted as one extrusion cycle after the zero cycle.

Figure 2:
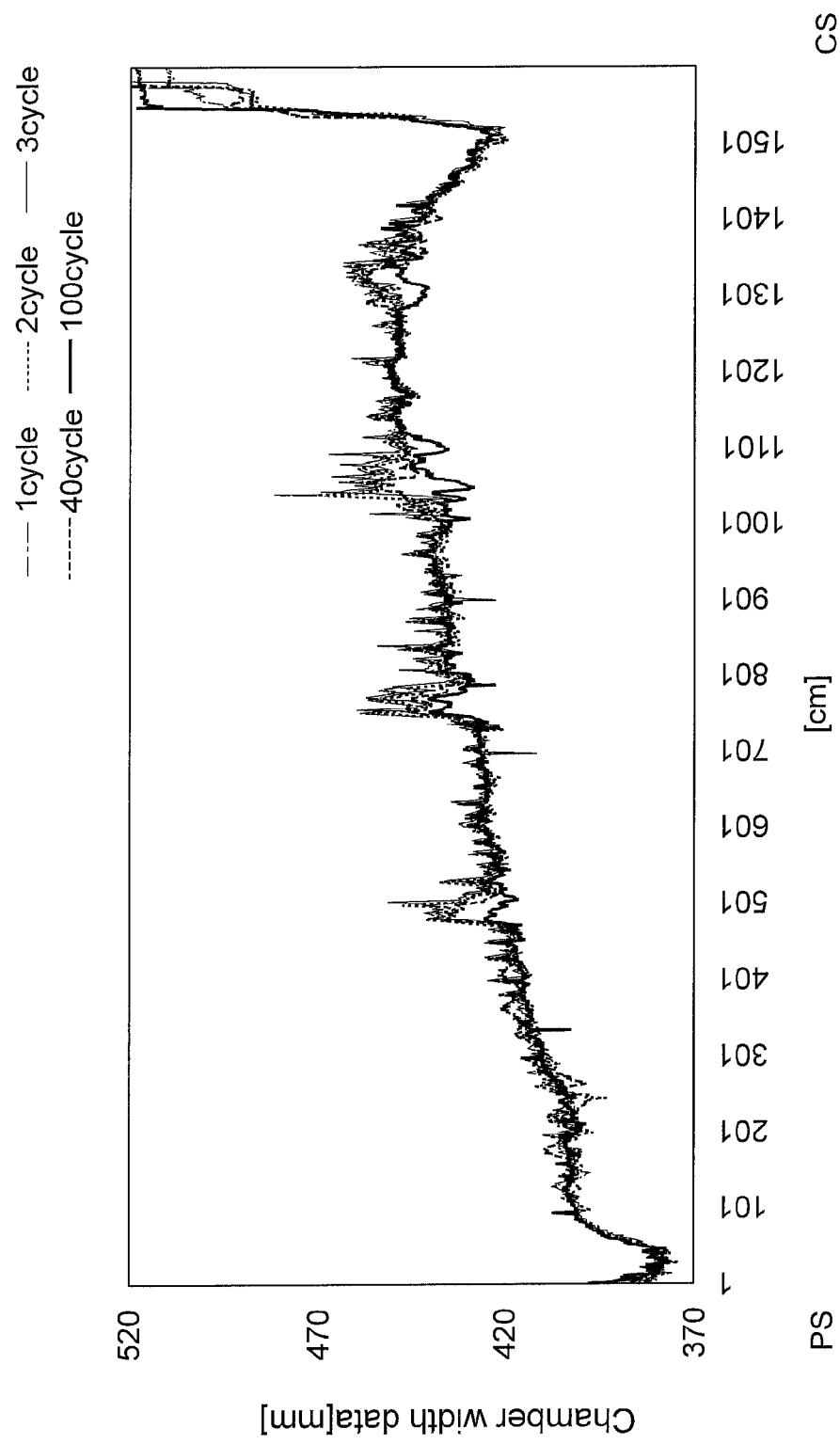
FIG. 2 is a graph indicating measurement results of chamber widths measured by a chamber width measurement device according to the present invention.

FIG. 2 is a graph indicating measurement results of chamber widths measured by the chamber width measurement device 6.

In this graph, the transverse axis indicates positions between the PS carbonization chamber port and the CS carbonization chamber port, with the PS carbonization chamber port being set at 0 cm. The ordinate axis indicates chamber width data (mm).

The chamber width data in the graph collectively indicates chamber widths obtained in the first, second, third, 40th, and 100th cycles.

Figure 3:
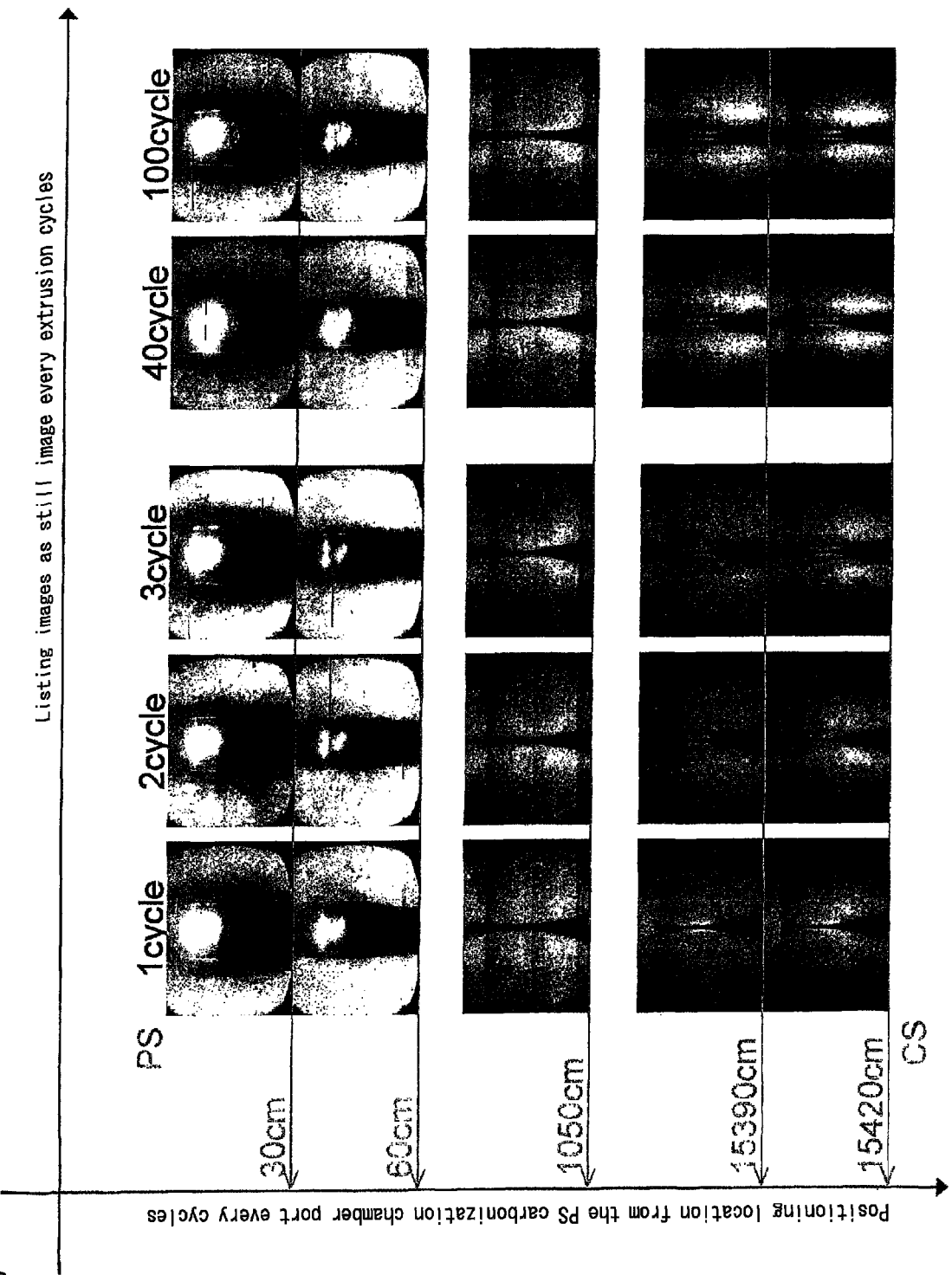
FIG. 3 is an explanatory view showing chamber wall images in respective extrusion cycles photographed with use of an in-chamber observation device according to the present invention.
Figure 4:
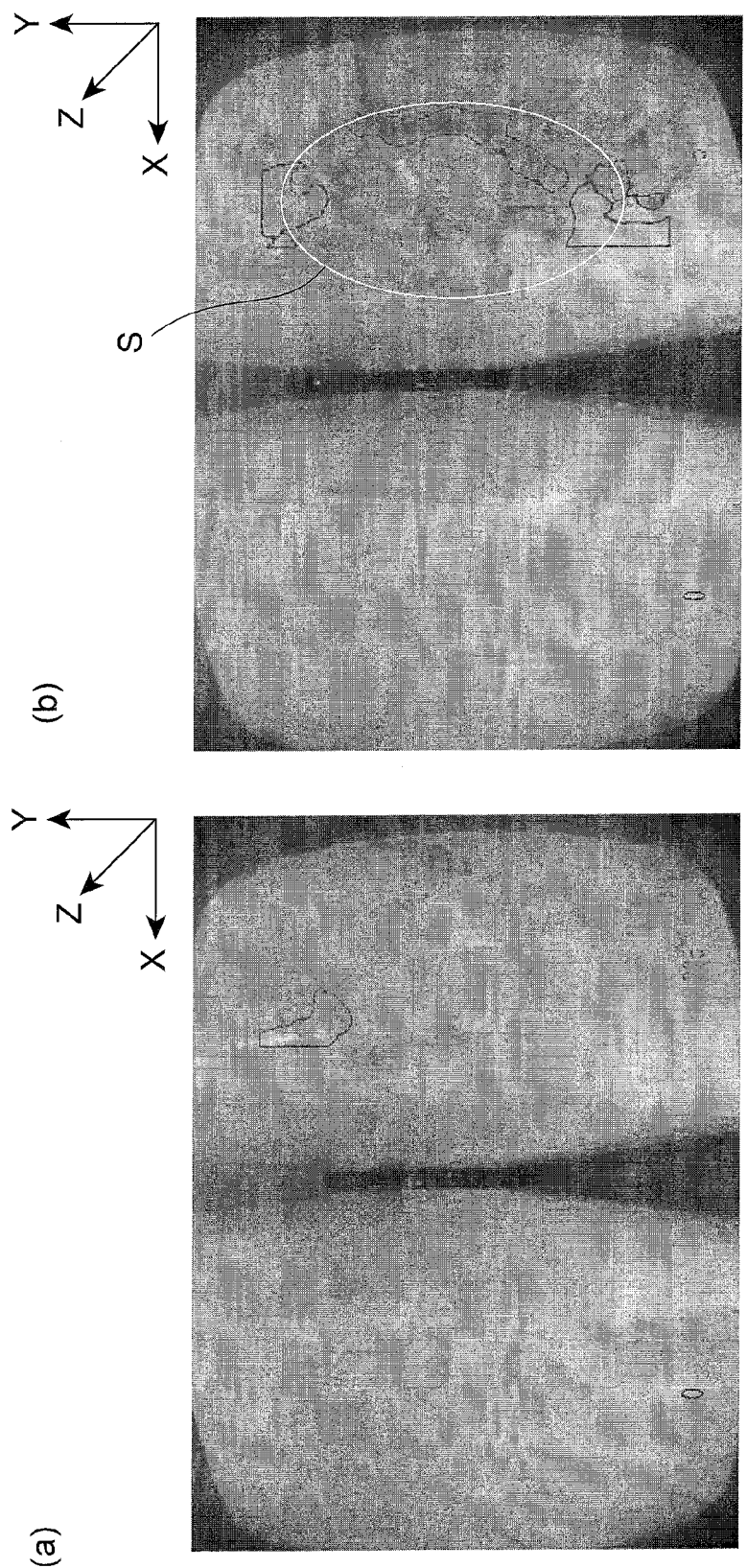
FIGS. 4(a) and 4(b) are chamber wall images used for calculation of an area of a changed portion in the state of the chamber wall.
Figure 5:
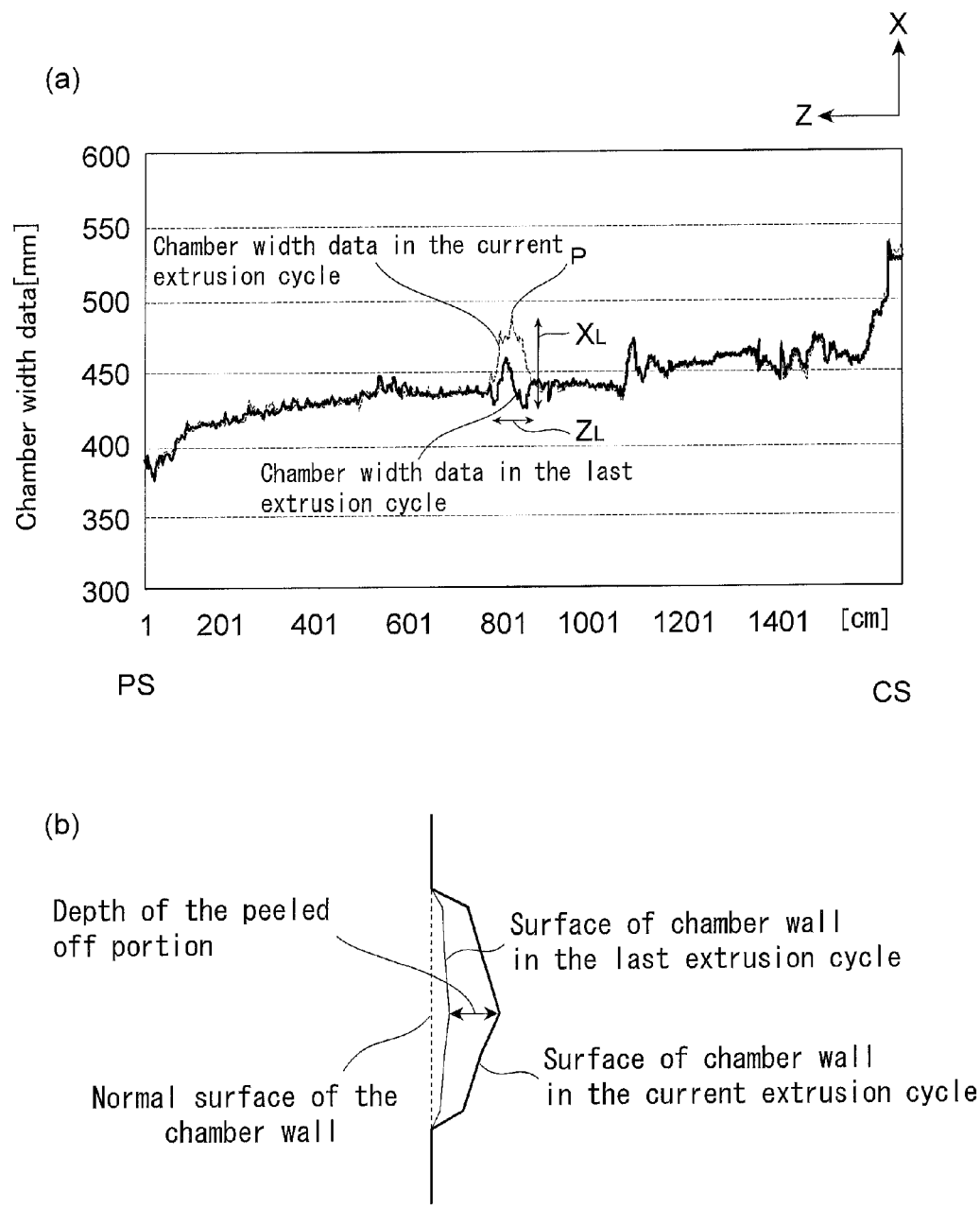
FIG. 5(a) is a graph of chamber width data used for calculation of a depth and a range of the changed portion in the state of the chamber wall.
FIG. 5(b) is an explanatory view showing a depth of a peeled off portion on the chamber wall.

FIG. 3 is an explanatory view showing chamber wall images in respective extrusion cycles photographed with use of the in-chamber observation device 7.

In this view, the extrusion cycles are indicated in the transverse direction (so as to correspond to the first, second, third, 40th, and 100th cycles in the graph of FIG. 2), while the positions between the PS carbonization chamber port and the CS carbonization chamber port are indicated in the ordinate direction. The PS carbonization chamber port is set at 0 cm.

In this manner, between chamber width data thus measured and chamber wall image data thus photographed between the PS carbonization chamber port and the CS carbonization chamber port, chamber width measurement positions and image extraction positions are matched in the respective extrusion cycles, on the basis of positional information outputted from the encoder 8.

Thereafter, as to be described below, finite differences are calculated between pieces of chamber width data measured at the same locations as well as between pieces of chamber wall image data photographed at the same locations in the respective extrusion cycles.

2.1 Numerical Conversion of Chamber Width Data

The measurement results are obtained as numerical values in the measurement of chamber widths. Thus, comparison is made between pieces of chamber width data at the same position in two different cycles to obtain a finite difference.

2.1.1 For Detection of Abnormality

By obtaining (chamber width data measured in the current cycle)−(chamber width data measured in the last cycle) such as (the second cycle)−(the first cycle), (the third cycle)−(the second cycle), . . . , or (the 40th cycle)−(the 39th cycle), a changed amount in chamber width at the same location is numerically converted.

2.1.2 For management of Tendency

By obtaining (chamber width data measured in the current cycle)−(arbitrary reference chamber width data/chamber width data in a specific extrusion cycle) such as (the second cycle)−(the first cycle), (the third cycle)−(the first cycle), or (the fourth cycle)−(the first cycle), a chronological change in chamber width is numerically converted.

2.2 Numerical Conversion of Chamber Wall Image Data

In accordance with the image analysis technique disclosed in JP-A-2009-57491 previously filed by the applicants of the present application, as to chamber wall image data obtained by photographing chamber walls, comparison is made in terms of the area between images of the same location in two different extrusion cycles to numerically convert a finite difference therebetween.

More specifically, by reading chamber wall image data in the current cycle, specifying the analysis range, calculating an average degree of brightness of the chamber wall image data in the current cycle, reading chamber wall image data at the same location in the last cycle, specifying the analysis range, calculating an average degree of brightness of the chamber wall image data in the last cycle, matching the degree of brightness of the chamber wall image data in the current cycle to the degree of brightness of the chamber wall image data in the last cycle, obtaining an areal finite difference between the chamber wall image data in the current cycle and the chamber wall image data in the last cycle, and calculating a region of the area having values not less than a predetermined value, in this order, an areal finite difference is obtained and the change in the state of the chamber wall is numerically converted.

2.2.1 For Detection of Abnormality

By obtaining an areal finite difference from calculation of (chamber wall image data in the current cycle)−(chamber wall image data in the last cycle) such as (the second cycle)−(the first cycle), (the third cycle)−(the second cycle), . . . , or (the 40th cycle)−(the 39th cycle), the change in the state of the chamber wall is numerically converted.

2.2.2 For Management of Tendency

By obtaining an areal finite difference from calculation of (chamber wall image data in the current cycle)−(arbitrary reference chamber wall image data/chamber wall image data in a specific extrusion cycle) such as (the second cycle)−(the first cycle), (the third cycle)−(the first cycle), or (the fourth cycle)−(the first cycle), a tendency of the change in the state of the chamber wall is numerically converted.

In these manners, the state of the chamber wall is numerically converted with use of chamber width data measured by the chamber width measurement device 6 and chamber wall image data photographed by the in-chamber observation device 7.

In other words, the area of a peeled off portion is calculated from chamber wall image data, and the depth or the like of the peeled off portion is calculated from chamber width data. It is therefore possible to grasp gouging or thickening of the chamber wall due to adhesion and growth of carbon at the measurement point.

More specific description is made with reference to FIGS. 4(a) to 5(b).

FIGS. 4(a) and 4(b) are chamber wall images used for calculation of the area of the changed portion in the state of the chamber wall. FIG. 4(a) shows the chamber wall image in the last cycle, while FIG. 4(b) shows the chamber wall image in the current cycle.

In each of FIGS. 4(a) and 4(b), the PS carbonization chamber port is shown on the back side of the chamber wall image, while the CS carbonization chamber port is shown on the front side of the chamber wall image. Set in correspondence with these chamber wall images are the Z axis in the horizontal direction along the length of the carbonization chamber (extrusion direction), the Y axis in the vertical direction, and the X axis along the width of the carbonization chamber.

In FIG. 4(b), a range S surrounded with an ellipse indicates an area of a peeled off portion where carbon is peeled off. In accordance with the image analysis technique disclosed in JP-A-2009-57491 referred to earlier, the peeled off portion is numerically converted to obtain an area of the peeled off portion in the Z-Y plane.

FIG. 5(a) is a graph of chamber width data used for calculation of the depth and the range of the changed portion in the state of the chamber wall. This graph, in which the transverse axis indicates the Z axis and the ordinate axis indicates the X axis, indicates chamber width data in the last cycle as well as chamber width data in the current cycle.

The chamber walls opposite to each other are provided so as to gradually expand from the PS carbonization chamber port to the CS carbonization chamber port. Accordingly, the graph of chamber width data draws lines generally slanted upward toward the CS carbonization chamber port. However, chamber width data has a peak where carbon is peeled off the chamber wall. In this graph, the chamber width data in the current cycle has a larger peak P as compared with the chamber width data in the last cycle.

As to the peak P, a distance $Z_L$ along the Z axis and a distance $X_L$ along the X axis are calculated to obtain the depth of the peeled off portion from the distance $X_L$ along the X axis (see FIG. 5(b)).

Furthermore, an area S of the peeled off portion is obtained from the distance $X_L$ along the X axis and the chamber wall image data. With an assumption that the peeled off portion has a conical shape, the volume of the peeled off portion can be obtained from the area S.

Moreover, the range (diameter) of the peeled off portion can be checked from the distance $Z_L$ along the Z axis.

In these manners, by associating the analysis results obtained by analyzing chamber width data and chamber wall image data that are obtained in the two different extrusion cycles, the monitoring system according to the present invention can quantitatively calculate the change in the state of the chamber wall with excellent accuracy, as the depth, the area, and the volume.

By managing the results together with operational information such as power used for extrusion, it is possible to grasp changes in the carbonization chamber, which may lead to operation troubles, as well as to chronologically observe such changes in the state of the chamber wall by means of numerical values.

Figure 6:
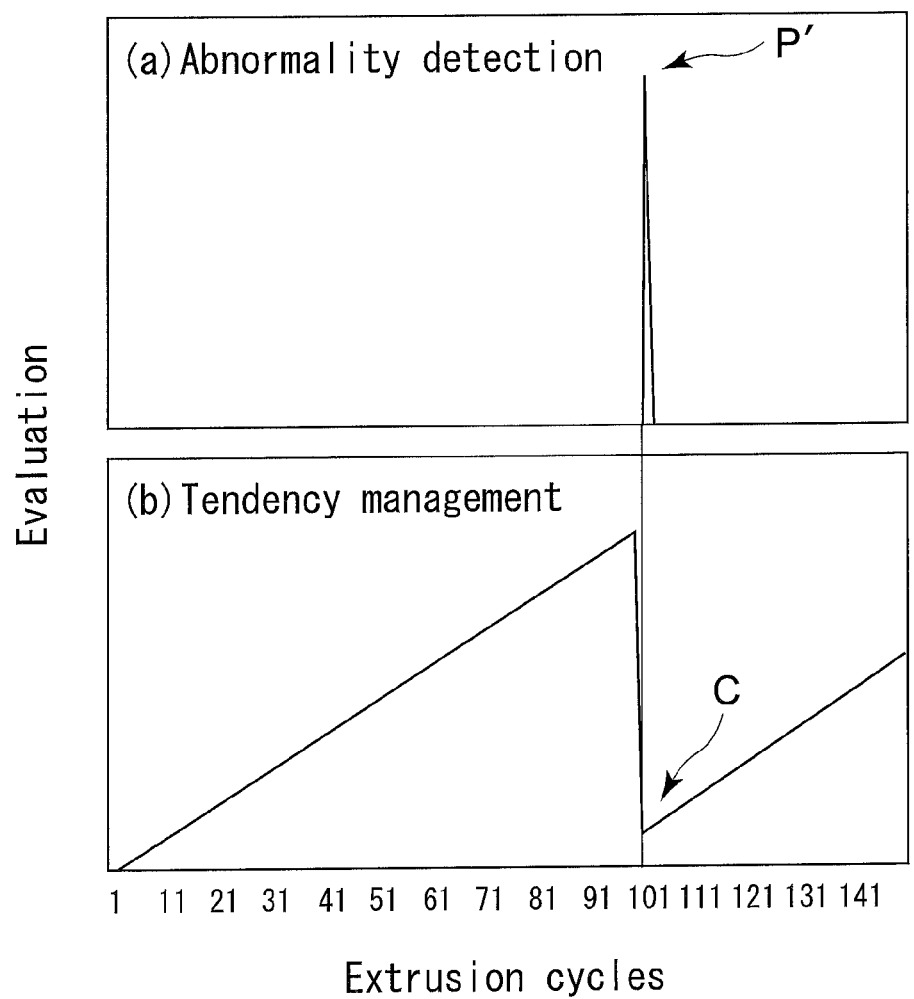
FIGS. 6(a) and 6(b) configure an explanatory view conceptually showing graphs of numerical transition used for abnormality detection (FIG. 6(a)) and tendency management (FIG. 6(b)) in accordance with an analysis result of the chamber width data and an analysis result of chamber wall image data.

FIGS. 6(a) and 6(b) configure an explanatory view conceptually showing graphs of numerical transition used for abnormality detection (FIG. 6(a)) and tendency management (FIG. 6(b)) in accordance with the analysis results of chamber width data and the analysis results of chamber wall image data. In this view, carbon is assumed to be peeled off in the 101st cycle.

The analysis results of chamber width data and chamber wall image data are sequentially accumulated in the database (accumulation means) 11 shown in FIG. 1, and can be accessed from the terminal device 12.

The graph of FIG. 6(a) is used for abnormality detection, indicating the changes in the state of the chamber wall by means of the difference between the current cycle and the last cycle as to each of the cycles, which is obtained from the analysis results of chamber width data and chamber wall image data from the first cycle to the 150th cycle in the same carbonization chamber.

The graph from the first cycle to the 100th cycle indicates normal transition. Carbon gradually adheres to the chamber wall as the number of cycles increases. However, there is no significant change in the comparison between the last cycle and the current cycle. Accordingly, no numerical change is observed, and the graph indicates transition along the transverse axis.

If carbon having adhered to the chamber wall in the 100th (last) cycle is peeled off in the 101st (current) cycle, there is a significant change in the comparison therebetween, and thus detected is a numerical peak P'.

In other words, the chamber width data and the chamber wall image data obtained in the current extrusion cycle is remarkably changed from the chamber width data and the chamber wall image data obtained in the past (last) extrusion cycle. Therefore, determination of an chamber wall abnormality can be made depending on whether or not the changes exceed predetermined values for chamber widths and chamber wall images.

In and after the 102nd cycle, carbon starts to adhere to grow again at the location where carbon has been peeled off. However, such adhesion and growth occur gradually and no significant change is observed in the comparison between the current cycle and the last cycle. Therefore, the graph indicates transition along the transverse axis, similarly to the graph showing transition from the first cycle to the 100th cycle.

The graph of FIG. 6(b) is used for management of a tendency in the state of the chamber wall.

It is assumed that carbon is peeled off in the 101st cycle. The graph indicates the changes in the state of the chamber wall by means of the difference between the current cycle and the last cycle as to each of the cycles, which is obtained from the analysis results of chamber width data and chamber wall image data from the first cycle to the 150th cycle in the same carbonization chamber.

The first cycle in this case is set subsequently to repair (specific extrusion cycle) and is assumed to have a reference value (reference data). The reference value can be set arbitrarily.

The graph indicates normal transition from the first cycle to the 100th cycle. Carbon gradually adheres to the chamber wall as the number of cycles increases. The change between the first cycle (reference value) and the current cycle is larger as the number of cycles increases. Therefore, the graph indicates transition slanted upward.

When carbon having adhered to the chamber wall is peeled off in the 101st (current) cycle, the numerical value in the current cycle approximates the numerical value in the first cycle (reference value). As a result of the comparison therebetween, there is observed only a slight difference from the reference value, so that the graph indicates significant decrease (see reference sign C).

In other words, the chamber width data and the chamber wall image data obtained in the current extrusion cycle are remarkably changed from pieces of chamber width data and pieces of chamber wall image data that are accumulated by obtaining in the past extrusion cycles (reference data).

FIG. 6(b) can be used not only for tendency management but also for determination of an chamber wall abnormality depending on whether or not the values exceed different predetermined values for chamber widths and chamber wall images.

It is also possible to grasp the degree of progress of deterioration of the chamber wall from the slant of the graph, thereby realizing tendency management on the state of the chamber wall.

In and after the 102nd cycle, carbon starts to adhere to grow again at the location where carbon has been peeled off. Therefore, the numerical value increases similarly to the transition from the first cycle to the 100th cycle.

The graphs in FIGS. 6(a) and 6(b) are indicated in a collective manner because these graphs draw similar lines, although absolute values and numerical units are different from each other between the case of using the analysis results of chamber width data and the case of using the analysis results of chamber wall image data.

3. Operation of the Monitoring System to See Inside the Camber of the Coke Oven

Figure 7:
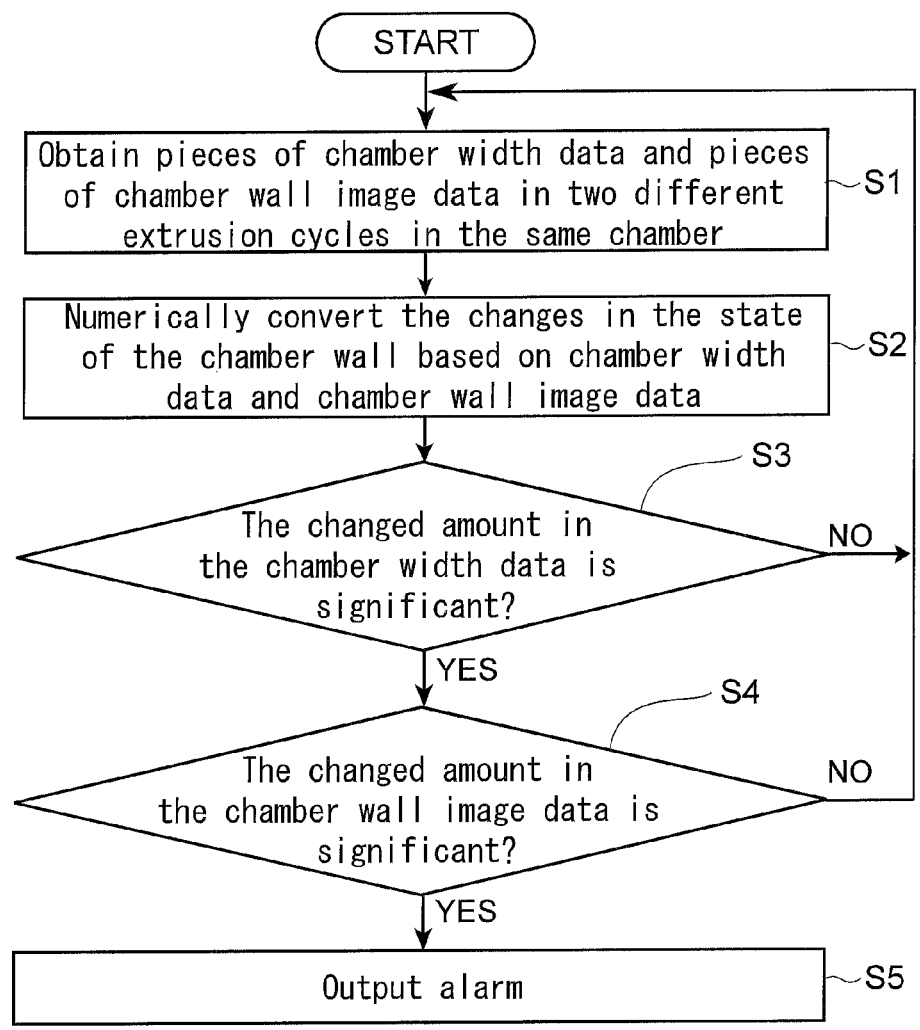
FIG. 7 is a flowchart showing control processes of the monitoring system to see inside the camber of the coke oven according to the present invention.

FIG. 7 is a flowchart showing control processes of the monitoring system to see inside the camber of the coke oven.

In this flowchart, the chamber width/chamber wall image data analysis and processing unit 10b initially obtains pieces of chamber width data and pieces of chamber wall image data in two different extrusion cycles at the same location in the same carbonization chamber (step S1).

Subsequently, a finite difference between the pieces of chamber width data and a finite difference between the pieces of chamber wall image data in the two extrusion cycles are obtained respectively to numerically convert the changes in the state of the chamber wall (step S2).

Calculated from the chamber width data is the distance in the X direction indicative of the depth of the peeled off portion. The volume of the peeled off portion may be calculated from the depth of the peeled off portion obtained from chamber width data and the area S obtained from chamber wall image data.

The chamber width data thus numerically converted is compared with the predetermined value for chamber width data to determine whether or not the numerical change is significant, in other words, the changed amount in the chamber width data exceeds the predetermined value for chamber width data (step S3). If NO as a result of the determination, the operation returns to step S1 to obtain next chamber width data and chamber wall image data.

If the changed amount in chamber width data is significant, it is further determined whether or not the numerically changed amount in chamber wall image data, in other words, the areal change in the damaged region on the chamber wall, exceeds the predetermined value for chamber wall image data (step S4). If NO as a result of the determination, the operation returns to step S1 to obtain next chamber width data and chamber wall image data.

If the changed amount in chamber wall image data is significant, an alarm is reported (outputted) (step S5).

In the processing described above, in a case where the changed amount only in chamber width data remarkably exceeds the predetermined value, it is regarded that severe damage occurs only in a small area, with no alarm being reported.

In a case where the changed amount only in chamber wall image data remarkably exceeds the predetermined value, it is regarded that a large area is damaged by a small depth, with no alarm being reported.

In the above control processes, as the method of determining an chamber wall abnormality, a finite difference between pieces of chamber width data and a finite difference between pieces of chamber wall image data in two extrusion cycles are obtained and numerically converted to compare with the predetermined values, respectively. However, the determination method is not limited thereto. Alternatively, the values in the 0 extrusion cycle subsequent to repair are set as reference values, and it is possible to determine as normal if chamber width data and chamber wall image data obtained in the current extrusion cycle are increased by constant values from the reference values, respectively, while it is possible to determine as having an chamber wall abnormality if these pieces of data are increased by more than the constant values, respectively.

In the present invention, it is possible to adopt a known data analysis technique other than (a) abnormality detection and (b) tendency management, as long as being possible to grasp the changed amounts.

Furthermore, in FIG. 7, steps S3 and S4 may be performed in the inversed order.

Moreover, in FIG. 1, the chamber width measurement device 6, the in-chamber observation device 7, and the encoder 8 can be provided at any positions, as long as being shiftable along with the extrusion ram 4. The monitor 15 is not essential.

4. Specific Example of Determination of Chamber Wall Abnormality

TABLE 1

Date/Month/Year: 1 Jun. 2010

| No. | Extrusion time (Date/Month/Year) | Chamber No. | Last Extruder No. | Extruder No. | Changed amount of chamber wall image data (average) | Changed amount of chamber width data (average) | PC peeling determination | | |
|---|---|---|---|---|---|---|---|---|---|
| | | | | | | | Image peak | Chamber width peak | determination |
| 5 | 01.06.2010 0:43 | 50 | 3 | 3 | 64.45833333 | 2.5 | ○ | | |
| 18 | 01.06.2010 2:30 | 115 | 3 | 3 | 94.29166667 | 254 | ○ | ○ | ○ |
| 30 | 01.06.2010 4:28 | 52 | 3 | 3 | 71.45833333 | 25.75 | ○ | | |
| 77 | 01.06.2010 12:47 | 41 | 3 | 3 | 99.29166667 | −88.25 | ○ | | |
| 78 | 01.06.2010 12:53 | 46 | 3 | 3 | 74.58333333 | 1.5 | ○ | | |
| 80 | 01.06.2010 13:08 | 56 | 3 | 3 | 136.1666667 | 296.25 | ○ | ○ | ○ |
| 116 | 01.06.2010 18:37 | 108 | 3 | 3 | 71.875 | 33.25 | ○ | | |
| 118 | 01.06.2010 18:53 | 118 | 3 | 3 | 90.70833333 | −13.5 | ○ | | |
| 126 | 01.06.2010 20:38 | 35 | 3 | 3 | 99.5 | 21.25 | ○ | | |
| 146 | 01.06.2010 23:32 | 17 | 3 | 3 | 79.04166667 | −31.25 | ○ | | |

TABLE 2

Date/Month/Year: 2 Jun. 2010

| No. | Extrusion time (Date/Month/Year) | Chamber No. | Last Extruder No. | Extruder No. | Changed amount of chamber wall image data (average) | Changed amount of chamber width data (average) | PC peeling determination | | |
|---|---|---|---|---|---|---|---|---|---|
| | | | | | | | Image peak | Chamber width peak | determination |
| 4 | 02.06.2010 0:28 | 52 | 3 | 3 | 64.70833333 | −96 | ○ | | |
| 5 | 02.06.2010 0:36 | 57 | 3 | 3 | 85.75 | −15.75 | ○ | | |
| 10 | 02.06.2010 1:15 | 82 | 3 | 3 | 81.58333333 | 329.25 | ○ | ○ | ○ |
| 18 | 02.06.2010 2:30 | 122 | 3 | 3 | 94.875 | −2.25 | ○ | | |
| 19 | 02.06.2010 2:39 | 127 | 3 | 3 | 80.79166667 | −26.25 | ○ | | |
| 22 | 02.06.2010 3:13 | 14 | 3 | 3 | 91.20833333 | −14 | ○ | | |
| 26 | 02.06.2010 3:46 | 36 | 3 | 3 | 155.4583333 | 378.25 | ○ | ○ | ○ |
| 67 | 02.06.2010 10:35 | 116 | 3 | 3 | 340.8333333 | −4.25 | ○ | | |
| 70 | 02.06.2010 11:24 | 3 | 3 | 3 | 80.54166667 | 31 | ○ | | |
| 83 | 02.06.2010 13:14 | 20 | 3 | 3 | 477.7083333 | — | ○ | | |
| 90 | 02.06.2010 14:08 | 70 | 3 | 3 | 493.8333333 | — | ○ | | |
| 126 | 02.06.2010 20:25 | 37 | 3 | 3 | 76.04166667 | 66.25 | ○ | | |

TABLE 3

Date/Month/Year: 3 Jun. 2010

| No. | Extrusion time (Date/Month/Year) | Chamber No. | Last Extruder No. | Extruder No. | Changed amount of chamber wall image data (average) | Changed amount of chamber width data (average) | PC peeling determination | | |
|---|---|---|---|---|---|---|---|---|---|
| | | | | | | | Image peak | Chamber width peak | determination |
| 26 | 03.06.2010 4:20 | 41 | 3 | 3 | 195.5416667 | 376 | ○ | ○ | ○ |
| 28 | 03.06.2010 4:36 | 51 | 3 | 3 | 60.95833333 | 9 | ○ | | |
| 31 | 03.06.2010 4:58 | 66 | 3 | 3 | 74.25 | 90.5 | ○ | | |
| 42 | 03.06.2010 6:23 | 121 | 3 | 3 | 76.58333333 | 40.5 | ○ | | |
| 60 | 03.06.2010 9:36 | 88 | 3 | 3 | 115.5416667 | 361 | ○ | ○ | ○ |

TABLE 3-continued

Date/Month/Year: 3 Jun. 2010

| No. | Extrusion time (Date/ Month/Year) | Chamber No. | Last Extruder No. | Extruder No. | Changed amount of chamber wall image data (average) | Changed amount of chamber width data (average) | PC peeling determination | | |
|---|---|---|---|---|---|---|---|---|---|
| | | | | | | | Image peak | Chamber width peak | determination |
| 66 | 03.06.2010 10:44 | 118 | 3 | 3 | 91.08333333 | −118.75 | ○ | | |
| 67 | 03.06.2010 10:52 | 123 | 3 | 3 | 62.25 | −27.75 | ○ | | |
| 69 | 03.06.2010 11:27 | 5 | 3 | 3 | 85.04166667 | −44 | ○ | | |
| 112 | 03.06.2010 18:14 | 102 | 3 | 3 | 93.625 | −4.5 | ○ | | |

Tables 1 to 3 indicate numerically converted average amounts of changes in chamber wall image data and average amounts of changes in chamber width data at the same location in the same carbonization chamber.

The changed amounts in chamber wall image data are extracted so as to exceed a predetermined value 50 for chamber wall image data. In the present embodiment, all the exemplified pieces of chamber wall image data are determined to have large changed amounts.

On the other hand, the changed amounts in chamber width data are extracted (colored portion) so as to exceed a predetermined value 200 for chamber width data. In the determination for the operation on June 1, the numerical changes are determined as significant in pieces of chamber width data for the carbonization chamber No. 115 and the carbonization chamber No. 56.

The predetermined value for chamber wall image data and the set data for chamber width data are respectively provided after checking the previous relationship with power values for coke extrusion, under conditions obtained from the average changed amounts that do not affect the coke extrusion. The respective predetermined values are provided arbitrarily depending on the management method.

In the determination on peeling off by the chamber width/chamber wall image data analysis and processing unit 10b, an "image peak" indicates whether or not there is any peak relatively to an average value of areal changes in the state of the chamber wall. An "chamber width peak" indicates whether or not there is any peak relatively to an average value of changes in depth in the state of the chamber wall. "Determination" indicates whether or not there is any peak relatively to the both thereof. The location on the chamber wall having large numerical changes both in chamber width and in chamber wall image data was checked to find actual peeling off. It is, therefore, confirmed that the monitoring system to see inside the camber of the coke oven according to the present invention can quantitatively monitor a change in the state of the chamber wall with excellent accuracy.

In the above embodiment, the chamber width measurement device 6 and the in-chamber observation device 7 are provided separately from each other on the support stand 5. Alternatively, these devices can be accommodated in a single case so as to achieve unitization.

Figure 8:
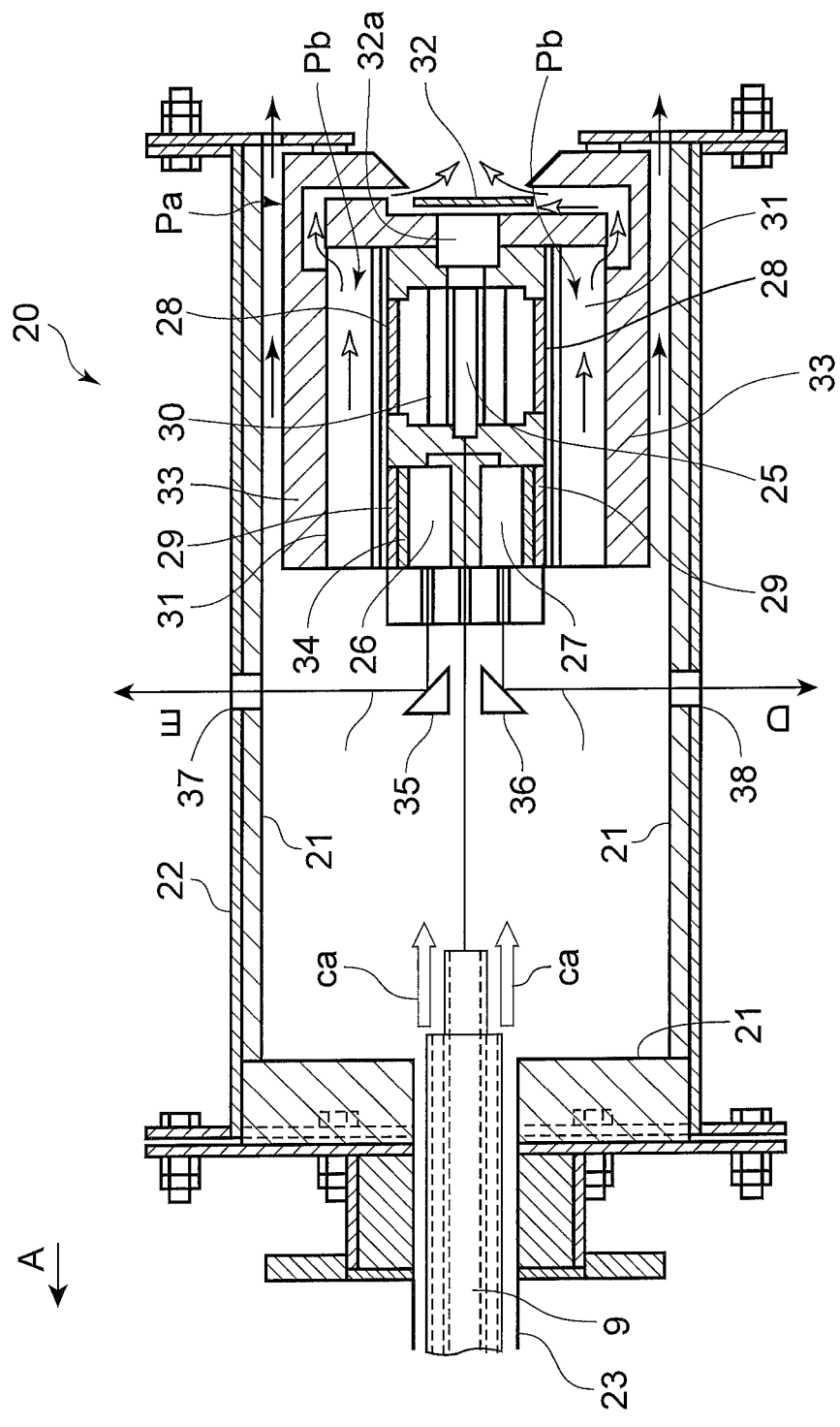
FIG. 8 is a planar sectional view of a measurement unit obtained by unitization of the chamber width measurement device and the in-chamber observation device.

FIG. 8 is a planar sectional view of a measurement unit that is obtained by unitization of the chamber width measurement device 6 and the in-chamber observation device 7.

In this view, a measurement unit 20 has a casing 22 that has a box shape and thermally insulated by a ceramic heat insulator 21. This casing 22 accommodates a CCD camera, a laser displacement sensor, a Peltier element serving as a thermoelectric cooling element, a thermocouple (not shown) used for temperature control, and the like, as to be described later.

The casing 22 has an end connected with a heat insulated pipe 23, through which cooling air ca is supplied into the casing 22. The heat insulated pipe 23 is also provided therein with the cable 9 used for transmission/reception of signals and supply of power. This cable 9 is connected with a CCD camera 25, laser displacement sensors 26 and 27, and Peltier element groups 28 and 29.

The CCD camera 25 is surrounded with heat conductors 30 made of aluminum blocks so as to be in close contact with the CCD camera 25. Each of the heat conductors 30 is surrounded with the Peltier element group 28 so as to be in close contact with the corresponding heat conductor 30. The Peltier element group 28 is further surrounded with a heat radiation fin group 31.

The respective Peltier elements configuring the Peltier element group 28 each have a plate shape and are double layered, having heat absorbing surfaces facing the CCD camera 25 and heat radiating surfaces facing the heat radiation fin group 31. In this configuration, the surface temperature of the CCD camera 25 itself can be controlled by the Peltier element group 28 by way of the heat conductors 30.

There is also provided a heat-resistant glass plate 32 in front in the photographing direction of the CCD camera 25. The heat-resistant glass plate 32 has an inner portion 32a in which an infrared absorbing filter, an infrared reflecting filter, and the heat-resistant glass are combined together with spacers being respectively interposed therebetween.

A camera unit, which has a cooling function and includes the CCD camera 25, the heat conductors 30, the Peltier element group 28, and the heat radiation fin group 31, is accommodated in a heat insulating cylinder 33 that is further accommodated in the casing 22. Accordingly, there is formed a cooling passage Pa between the outer wall of the heat insulating cylinder 33 and the inner wall of the casing 22. There is also formed a cooling passage Pb in a gap between adjacent fins in the heat radiation fin group 31. Streams of cooling air ca having flown through the cooling passages Pb join together at the center of the heat-resistant glass plate 32 and are discharged out of the casing 22.

The laser displacement sensors 26 and 27 each have a known configuration including a light emitting element and a light receiving element each made of a semiconductor laser and accommodated in a case. The laser displacement sensors 26 and 27 emit laser beams in the chamber width direction (along arrows D and E), to partially detect reflected beams with use of the light receiving elements, respectively.

The laser displacement sensors 26 and 27 are surrounded with heat conductors 34 made of a material same as that for the heat conductors 30 so as to be in close contact with the laser displacement sensors 26 and 27. The heat conductors 34 are surrounded with the Peltier element group 29 configured in the same manner as the Peltier element group 28 so as to be in close contact with the heat conductors 34. The Peltier element group 29 is further surrounded with the heat radiation fin group 31.

The laser displacement sensors 26 and 27 are respectively provided with reflecting mirrors 35 and 36 at light emitting ends. These reflecting mirrors 35 and 36 redirect by 90 degrees laser beams T and T, which pass through measurement windows 37 and 38, respectively, to be applied to the chamber wall.

In this manner, the chamber width measurement device 6 and the in-chamber observation device 7 thus unitized advantageously realize compact provision of the two devices.

Although the present invention has been fully described in connection with the preferred embodiment with reference to the accompanying drawings, the present invention can be embodied with various modifications and corrections by those skilled in the art. Such modifications and corrections are to be regarded as being included in the present invention as long as not departing from the technical range of the present invention.

INDUSTRIAL APPLICABILITY

The present invention is applicable to a management method for the chamber wall of the coke oven of monitoring the camber by measuring chamber width data in the camber and checking the state of the chamber wall.

DESCRIPTION OF REFERENCE SIGNS

1 Coke extruder
2 Ram head
3 Ram beam
4 Extrusion ram
5 Support stand
6 Chamber width measurement device
7 In-chamber observation device
8 Encoder (position detection means)
9 Cable
10 Computer
10a Chamber width/chamber wall image data extraction unit
10b Chamber width/chamber wall image data analysis and processing unit
10c Alarm output unit
11 Database
12 Terminal device
13 Signal/power cable
14 Signal cable
15 Monitor

The invention claimed is:

1. A method for monitoring inside a chamber of a coke oven comprising:
    obtaining pieces of chamber width data and pieces of chamber wall image data in different extrusion cycles at a same location in a same carbonization chamber in a coke oven;
    calculating and numerically processing a finite difference between the piece of chamber width data in a current extrusion cycle and the piece of chamber width data in a past extrusion cycle and a finite difference between an area of a chamber wall damaged portion in the current extrusion cycle and an area of a chamber wall damaged portion in the past extrusion cycle using the pieces of chamber wall image data;
    obtaining a conical volume of a changed portion of the chamber wall from a distance $X_L$ along an X axis obtained from the calculated and numerically processed finite difference from the pieces of chamber width data and an area S of a peeled off portion obtained from the calculated and numerically processed finite difference from the pieces of chamber wall image data; and
    determining a chamber wall abnormality in accordance with a change in the volume.

2. The method for monitoring inside the chamber of the coke oven according to claim 1, comprising:
    calculating and numerically processing the finite difference between the piece of chamber width data in the current extrusion cycle and the piece of chamber width data in the past extrusion cycle and the finite difference between the area of the chamber wall damaged portion in the piece of chamber wall image data in the current extrusion cycle and the area of the chamber wall damaged portion in the piece of chamber wall image data in the past extrusion cycle; and
    comparing the calculated and numerically processed finite difference from the pieces of chamber width data with a predetermined value for chamber width data, and comparing the calculated and numerically processed finite difference from the pieces of chamber wall image data with a predetermined value for chamber wall image data.

3. The method for monitoring inside the chamber of the coke oven according to claim 1, wherein an alarm is reported upon determination of the chamber wall abnormality.

4. A monitoring system to see inside a chamber of a coke oven comprising:
    a chamber width measurement device that measures a chamber width in a carbonization chamber of a coke oven;
    an in-chamber observation device that photographs a chamber wall in the carbonization chamber of the coke oven; and
    a computer that analyzes chamber width data measured by the chamber width measurement device and chamber wall image data photographed by the in-chamber observation device, the computer including:
    a chamber width/chamber wall image data extraction unit that extracts pieces of chamber width data and pieces of chamber wall image data in different extrusion cycles at a same location in a same carbonization chamber; and
    a chamber width/chamber wall image data analysis and processing unit that calculates a finite difference between the piece of chamber width data in a current extrusion cycle and the piece of chamber width data in a past extrusion cycle and a finite difference between an area of a chamber wall damaged portion in the current extrusion cycle and an area of a chamber wall damaged portion in the past extrusion cycle as a calculated finite difference between the pieces of chamber wall image data, and obtains a conical volume of a changed portion of the chamber wall, from a distance $X_L$ along an X axis obtained from an area S of a peeled off portion obtained from the calculated finite difference from the pieces of chamber width data and the calculated finite difference from the pieces of chamber wall image data, to detect a chamber wall abnormality and manage a tendency in accordance with a change in the volume.

5. The monitoring system to see inside the chamber of the coke oven according to claim 4, wherein the computer includes an alarm output unit that reports an alarm upon determination of the chamber wall abnormality.

6. The monitoring system to see inside the chamber of the coke oven according to claim 4, wherein the chamber width measurement device and the in-chamber observation device are provided on an extrusion ram at a same height, and the computer is connected with a position detection means for detecting a position of the extrusion ram.

7. The monitoring system to see inside the chamber of the coke oven according to claim 6, further comprising a database that stores the pieces of chamber width data and the pieces of chamber wall image data associated with positional information detected by the position detection means.

8. The method for monitoring inside the chamber of the coke oven according to claim 2, wherein an alarm is reported upon determination of the chamber wall abnormality.

9. The monitoring system to see inside the chamber of the coke oven according to claim 5, wherein the chamber width measurement device and the in-chamber observation device are provided on an extrusion ram at a same height, and the computer is connected with a position detection means for detecting a position of the extrusion ram.

* * * * *